(12) United States Patent
Blatt (10) Patent No.: US 7,128,763 B1
(45) Date of Patent: Oct. 31, 2006

(54) JOINT TREATING METHOD

(76) Inventor: Gerald Blatt, 2840 Long Beach Blvd., Long Beach, CA (US) 90806

( * ) Notice: Subject to any disclaimer, the term of this patent is extended or adjusted under 35 U.S.C. 154(b) by 0 days.

(21) Appl. No.: 09/289,000

(22) Filed: Feb. 25, 1997

Related U.S. Application Data (63) Continuation of application No. 08/452,227, filed on May 26, 1995, now abandoned.

(51) Int. Cl.
*A61F 2/30* (2006.01)
(52) U.S. Cl. .................................. 623/18.11; 623/908
(58) Field of Classification Search ................ 623/16, 623/18–23, 23.12, 23.14, 23.58
See application file for complete search history.

(56) References Cited

U.S. PATENT DOCUMENTS

| | | | |
|---|---|---|---|
| 5,007,934 A * | 4/1991 | Stone ........................... | 623/20 |
| 5,007,939 A * | 4/1991 | Delcommune et al. ....... | 623/16 |
| 5,207,712 A * | 5/1993 | Cohen ........................... | 623/21 |
| 5,306,311 A * | 4/1994 | Stone et al. ................... | 623/18 |
| 5,607,474 A * | 3/1997 | Athanasiou et al. .......... | 623/16 |
| 5,725,590 A * | 3/1998 | Maumy et al. ............ | 623/23.15 |
| 6,113,640 A * | 9/2000 | Tormala et al. .............. | 623/18 |

* cited by examiner

*Primary Examiner*—Paul B. Prebilic
(74) *Attorney, Agent, or Firm*—Townsend and Townsend and Crew LLP (57) ABSTRACT

A method for treating a non-weight bearing arthritic joint involves resecting at least one of the opposed joint surfaces to expose a cancellous bone surface. A bioresorbable implant is mounted to one of the joint surfaces so that the resected joint surface rubs against the surface of the implant. This causes the fibroblast to change into fibrocartilage at the resected bone surface as the implant is resorbed thereby effectively replacing the implant with fibrocartilage during such resorption.

9 Claims, 6 Drawing Sheets

(4 of 6 Drawing Sheet(s) Filed in Color)

JOINT TREATING METHOD

This is a Continuation of application Ser. No. 08/452,227 filed May 26, 1995, now abandoned.

BACKGROUND OF THE INVENTION

This invention is related to the pathological condition of arthritis. Arthritis is the wear and tear of the articular surface of the joint. "Arthro" means joint; "Itis" is inflammation. Normally the bone ends at the joint surfaces are covered with articular cartilage. This type of articular cartilage with which we are born is called hyaline cartilage and is smooth, is lubricated by synovial fluid, and in some people will wear more than a hundred years. In others, depending upon the quality of the cartilage which they have inherited, it will wear down exposing bone surface which then rubs against bone surface producing inflammation of the joint and thus the arthritis.

The most common form of arthritis is osteoarthritis which is the result of wear and tear of the cartilage with time and use. The cartilage may also be destroyed by a systemic disease such as rheumatoid arthritis or gout. The smooth, matching congruous articular surface may also be disrupted by trauma, either a fracture that goes through the joint surface, or an infection wearing away the cartilage. Nevertheless, the end result is the exposure of bone against bone which is painful, disabling and limits function.

Once the original hyaline cartilage with which we are born is destroyed, the joint is incapable of stimulating the regrowth of hyaline cartilage or growing any other type of articular cartilage. Therefore, various operative procedures are used to alleviate the pain and dysfunction associated with arthritis; these include fusion of the joint, thereby relieving the pain by completely stopping motion at the joint, and some type of arthroplasty reconstruction of the joint. This may be done by inserting some prosthetic material between the joint surfaces; a biological tissue, such as tendon graft or a strip of fascia, which is the tissue covering the muscle sleeve, may also be placed between the joint surfaces. There are obviously disadvantages to each of these alternatives as well as advantages. A fusion will result in permanent loss of motion. The biological tissue which is inserted will often degenerate into scar tissue and often will not wear well with stress. Various types of prosthetic implants are used, some more advantageous than others.

The carpometacarpal joint of the thumb, also called the basal joint of the thumb, is the only joint of the hand that we rotate. The joint is essentially saddle shaped, having not progressed in evolution as quickly as man has. Man is the only primate on earth that does rotate the thumb into opposition against the fingertips; therefore, we are constantly turning in the saddle. Depending upon the quality of cartilage, which is inherited, the stress to which it is often subjected will often cause the articular cartilage to wear down producing painful, grinding arthritis. Almost 10% of the population will be subject to this particular pathological entity.

Figure 1A:
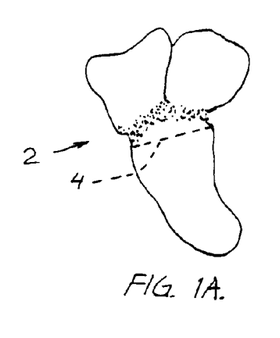
FIG. 1A illustrates an arthritic scapho-trapezial-trapezoidal joint of the hand with a line of resection indicated in dashed lines.
Figure 1B:
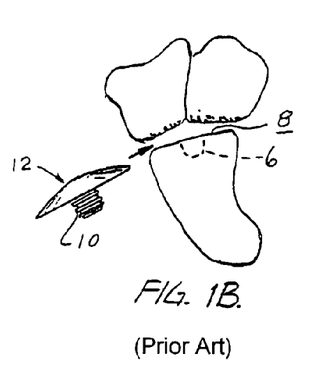
FIG. 1B illustrates the joint of FIG. 1A with a resected arthritic surface prepared for placement of a prior art non-resorbable, silicone rubber implant.
Figure 1C:
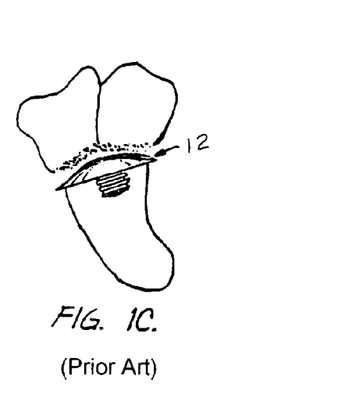
FIG. 1C shows the joint of FIG. 1B with the implant in place.
Figure 1D:
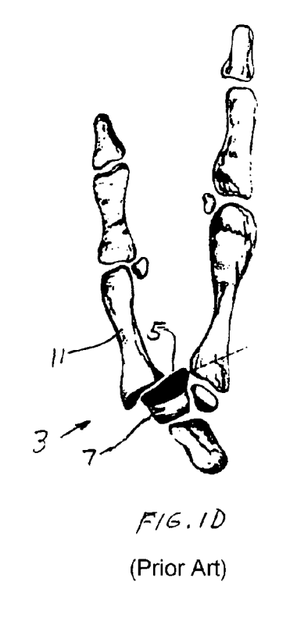
FIGS. 1D–1F show views similar to those of FIGS. 1A–1C but for an arthritic carpometacarpal joint.
Figure 1E:
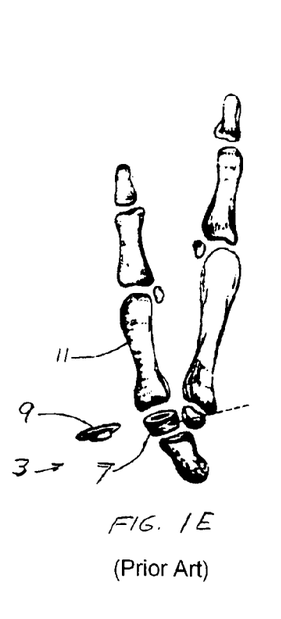
Figure 1F:
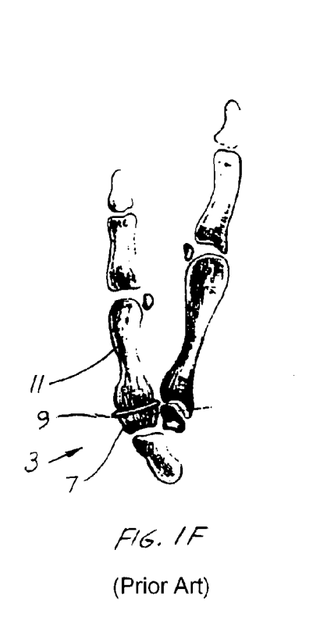
Figure 2:
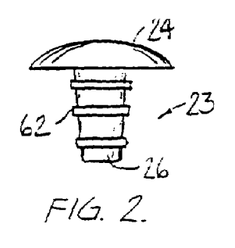
FIG. 2 is a side view of a bioresorbable implant made according to the invention.

Over 25 years ago, Dr. Charles R. Ashworth and I developed an arthroplasty for this joint in which we would use a wafer or disc-like implant made of a silicone rubber sold by Dow Corning as Silastic. Silastic has proven to be one of the most durable and best tolerated implant materials in the upper extremity and is often utilized for major joint replacements at the knuckle joints, the joints in the middle of the fingers, at times between the small ball-bearing or carpal bones of the wrist, and as stated, at the base of the thumb. We have used this Silastic interposition arthroplasty quite successfully for over 25 years. FIGS. 1A–1C illustrate treatment of arthritis at the scapho-trapezial-trapezoidal joint 2. FIG. 1A illustrates a line of resection 4 of the convex dome of the scaphoid. FIG. 1B shows the status following resection of the arthritic surface, including the preparation of a cylindrical recess 6 formed in the center of resected surface 8 for receipt of a stem 10 of an implant 12 made of Silastic. FIG. 1C illustrates the implant 12 in place. FIGS. 1D–1F illustrate a conventional treatment of an arthritic carpometacarpal joint 3 of the thumb. FIG. 1D shows the amount of the saddle or convex portion 5 to be resected from the trapezium 7. FIG. 1E shows the resected trapezium 7 prepared for accepting a hat-shaped implant 9; implant 9 is typically made of Silastic material. FIG. 1F shows implant 9 in place between the resected trapezium 7 and the base of the metacarpal 11.

While these procedures have been quite successful and have improved the quality of life for numerous people over the last 25 years, there have been some recent questions regarding the efficacy of continued use of any implant made of silicone rubber. Therefore, I gave thought and consideration as to what other type of material might be used as an interpositional implant.

As background to the development of the present invention, I conducted a review of reported cases of patients who have broken or worn away their Silastic implants. The joints of these patients, based on re-exploration conducted from a period of nine months to several years postoperatively, have been covered by a smooth, white, moistened, glistening surface in the area where there had previously been raw resected bone. Therefore, my postulation is that the original surgery, removing the arthritic spurs and the uneven joint surface, left a raw bony surface normally covered by a blood clot or hematoma which then came in contact with the inert, smooth Silastic disc. The gradual fibroplasia of the blood clot appears to progress to fibrocartilage. At times the surgical exploration of this surface tissue has been biopsied and has microscopically proven to be fibrocartilage.

Another important concept is the body's attempt to repair the joint surface with normal scar tissue. The basic cell of healing is called the fibroblast and will develop at any site of injury and is the transformation of a normal blood clot. The fibroblast will go through a series of histological microscopic changes called fibroplasia. The fibroblast on a surface where there is constant motion will change and develop into an entity known as fibrocartilage. This is white, smooth and looks very much like cartilage. It does not, however, have a basic property of hyaline cartilage, that is the ability to withstand impact stress. Therefore, fibrocartilage has been known to not survive the weight bearing stress of lower extremity joints, including the hip, the knee or the ankle. There have apparently been no studies of the competence or resilience of fibrocartilage as a joint surface for non-weight bearing, upper extremity joints.

SUMMARY OF THE INVENTION

The present invention is based on the recognition that an implant that would stimulate and promote the formation of fibrocartilage could be used at a resected arthritic joint. The fibrocartilage would be a durable and competent joint surface for relief of pain, maintaining motion and adequate functional performance in the non-weight bearing, typically upper extremity, joints. A bioresorbable implant is preferably inserted in the same fashion as the conventional Silastic wafer disc. The bioresorbable implant is placed between the resected joint surfaces and stimulates the formation of fibrocartilage as the bioresorbable implant is gradually dissipated and safely biologically resorbed by the body. These materials have been in use for many years as synthetic bioresorbable suture material, and are made of different polymers, such as PLA (polylactic acid) and other polymers in various combinations. This same material has also been utilized as a bioresorbable staple in certain types of shoulder reconstructions as well as knee ligament reconstruction.

The biological process of the resorption, called hydrolysis, is as follows: the bioresorbable material will dissipate to water and carbon dioxide and is eventually eliminated by the body primarily through the respiratory system. Depending upon the type of material, its duration and durability is altered. Many of the copolymers utilized in the resorbable sutures will disappear in anywhere from two to six weeks, although a pure polymer of rigid material could last for several years.

For the investigative studies the pure polymer of PLA was chosen. The concept was to resect the joint, place the implant of PLA against the surface, allow the joint to move and study whether the development of fibrocartilage would gradually fill the joint as the implant is resorbed, eventually yielding ideally a resurfaced, smooth, clean joint with no remaining implant material.

The investigative studies have proven that the use of bioresorbable PLA interpositional implants appears to stimulate fibrous metaplasia from an organized hematoma, to sophisticated fibrocartilage, to an almost "hyaline" matrix for non-weight bearing joints. The procedures employed are substantially the same as those employed with the wafer or disk-like implants made of silicone rubber used with various joints in the hand; however, the potential problems which can occur in some circumstances using silicone rubber interpositional implant materials are avoided.

Other features and advantages of the invention will appear from the following description in which the preferred embodiment and method have been set forth in detail in conjunction with the accompanying drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DESCRIPTION OF THE PREFERRED EMBODIMENT

Referring to FIGS. 2 and 3A–3F, the present invention is directed to a method for treating a joint surface, typically an arthritic joint surface, which uses a bioresorbable implant, such as implant 23, configured for positioning between articulated joint surfaces such as the opposing surfaces of a hand (finger) joint or a shoulder joint, e.g. between a surface 20 and a resected surface 34. At least one of the joint surfaces, e.g. resected surface 34, is an exposed cancellous joint surface.

The method of the present invention is therefore for treating at least one of two opposing, first and second, relatively movable joint surfaces by initially resecting the bone to form a cancellous bone surface. A bioresorbable implant, such as implant 23, is placed between the first and second surfaces to space them apart. The implant has at least one face which is opposite and shaped complementary to the opposing bone surface so that the implant can slidably move relative to the at least one of the first and second surfaces. By allowing the face of the implant to slidably move relative to the resected surface while promoting the growth of fibroblast on the cancellous surface for a sufficient time to allow the fibroblast to convert into fibrocartilage, the fibrocartilage generates a fresh, sliding joint surface. The implant maintains a spacing between the joint defining surfaces, and after the implant has resorbed, the fibrocartilage defines the joint surface.

The invention has been tested through an animal study, described below.

Figure 3A:
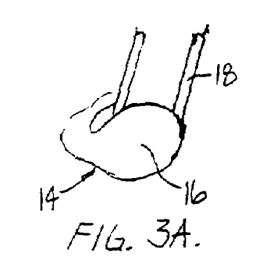
FIG. 3A illustrates the humoral head of a rabbit fore-limb shoulder joint with a sagittal saw removing a portion of the dome surface of the joint.
Figure 3B:
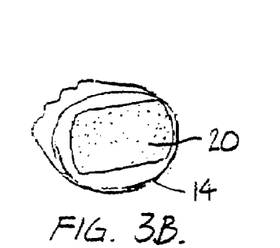
FIG. 3B illustrates a resected surface, with raw cancellous bone exposed, after the procedure of FIG. 3A.
Figure 3C:
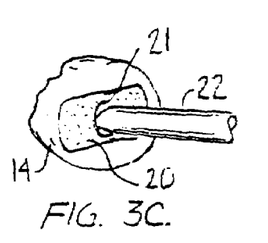
FIG. 3C shows the use of a power burr to form a cavity in the resected surface.

The New Zealand white rabbit was chosen for the research project, utilizing the fore-limb shoulder joint which is almost non-weight bearing. The rabbits were operated upon and studied in accordance with all guidelines of animal research experimental techniques. The shoulder joint was approached surgically, after the rabbit was anesthetized and under sterile conditions, and the head 14 of the humerus or round ball of the ball and socket shoulder joint was exposed. The distal convex, dome surface 16 of humeral head 14 was removed by a sagittal saw 18, as illustrated in FIG. 3A, to create a flat resected surface 20 with exposed raw or cancellous bone exposed; see FIG. 3B. A cavity 21 was then formed at about the center of resected surface 20 and into the medullary canal with a power burr 22 as shown in FIG. 3C. The PLA implant 23, having a head 24 and a stem 26 extending from a backside of the implant, as mounted to resected head 14 of the humerus with the round, domed head 24 of implant 23 with a face reconstituting the rounded surface of the humeral head, and stem 26 of implant 23 locking into cavity 21 formed in the medullary canal of the humerus. See FIGS. 3D and 3E.

Figure 3D:
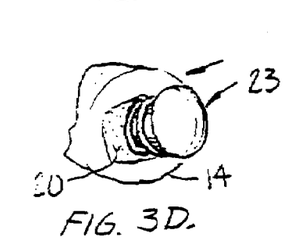
FIG. 3D shows the act of inserting the implant of FIG. 2 into the cavity formed in the medullary canal of the humoral head created in the step shown in FIG. 3C.
Figure 3E:
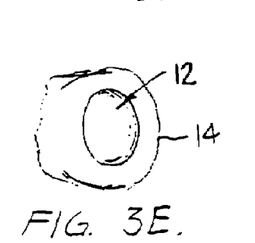
FIG. 3E shows the humoral head of FIG. 3D after the insert has been fully mounted thereto.
Figure 3F:
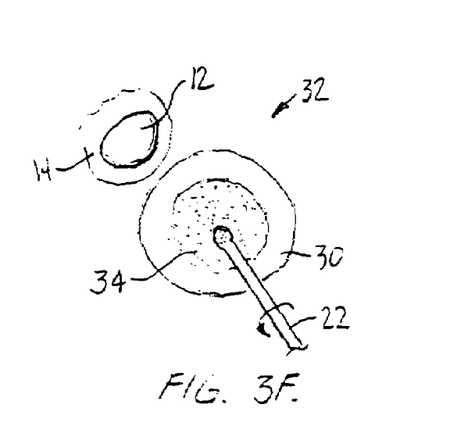
FIG. 3F shows a portion of the shoulder joint with the humoral head of FIG. 3E adjacent the glenoid fossa with a power burr used to create a concave resected surface for engagement with the convex head of the implant mounted to the humoral head of FIG. 3E; all articular cartilage is thus removed.

Attention is now directed to FIG. 3D and to the concave surface 30 of the shoulder joint 32 (see FIG. 3F) called the glenoid fossa (this being the other surface of the ball and socket joint, that is, the socket portion). Again using power driven burr 22, the normal articular cartilage on joint surface 30 was removed down to raw subchondral or cancellous bone to create a concave resected joint surface 34. The dislocated shoulder joint was then reduced, that is, brought back together with head 24 of implant 23 abutting resected surface 34. The wound was then closed. Implant 23 brought into direct contact with this raw socket surface 34 simulated an arthritis. Therefore, head 24 of implant 23 would move against this raw bony surface 34 and the rabbits would then be studied at varying intervals.

A total of eighteen rabbits were operated upon, maintained and studied over the next two years. The post-operative findings were that there were no infections, the rabbits maintained joint mobility and no altered gait was observed for any of the rabbits. The rabbits were retrieved and sacrificed at varying periods postoperatively: these being one year, a year and a half and two years. The shoulder joints were retrieved and studied by gross examination. Microscopic evaluation of the altered joint surface was also made. On gross examination, there was noted to be a smooth, white surface where there had been raw cancellous or subchondral bone at the time of the original surgery. The PLA implant had gradually resorbed at varying degrees, depending upon the time postoperatively.

In the one-year rabbit studies there was still noted to be a small amount of sterile synovitis about the margins of the joint, but at 18 months and 24 months there was no evidence of this synovitis. The smooth surface of the joint had progressed to gross inspection.

Figure 5:
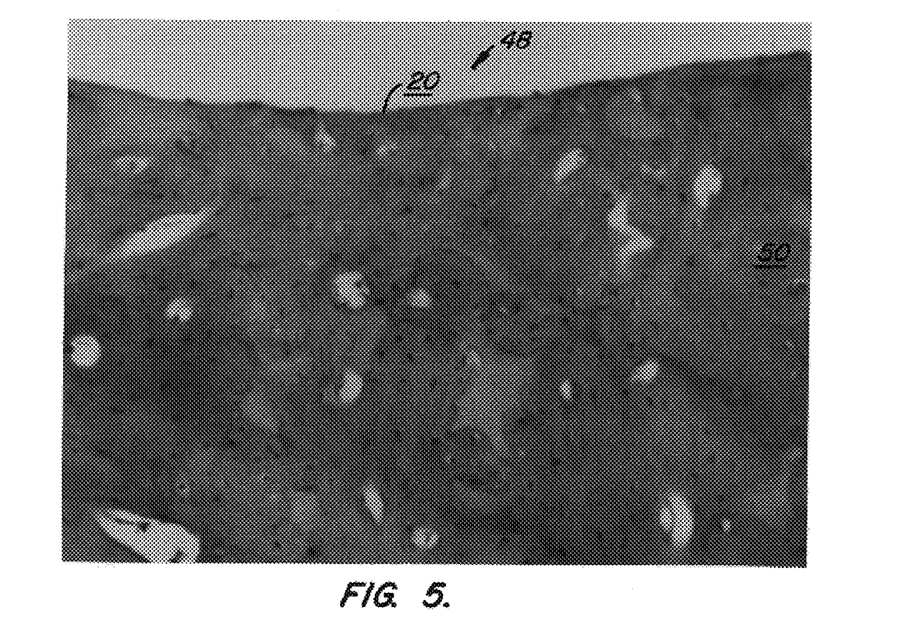
FIG. 5 is a photomicrograph, in cross-section, illustrating a glenoid articular surface after resection with all the cartilage removed.
Figure 6:
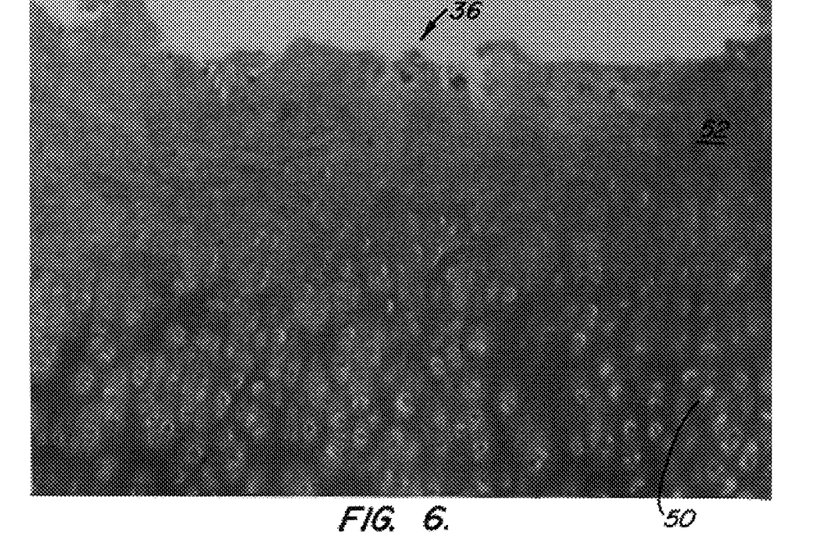
FIGS. 6 and 6A are cross-sectional and scanning photomicrographs of a glenoid articular surface of a rabbit sacrificed 12 months after the procedure of FIGS. 3A–3F showing some evidence of synovitis and only patchy areas of fibroplasia in FIG. 6A with patchy areas shown in FIG. 6 which suggest fibroblastic activity with early metaplasia to immature fibrocartilage.
Figure 7:
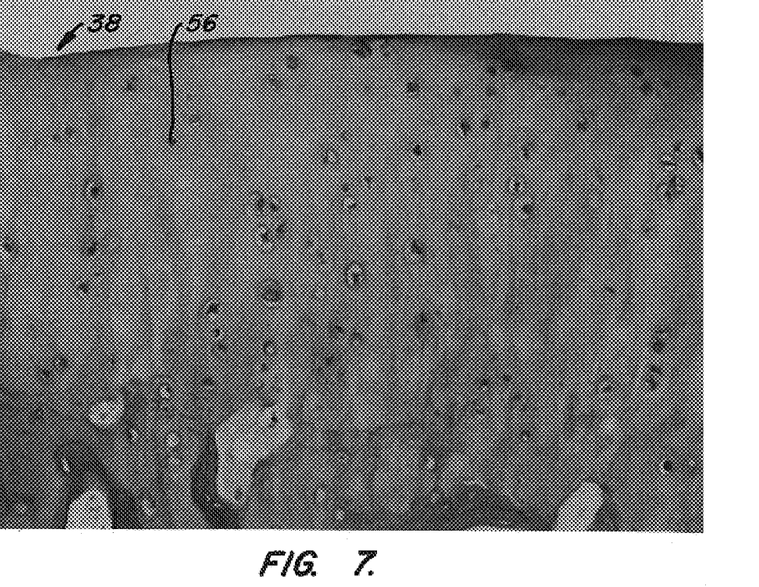
FIGS. 7 and 7A are similar to FIGS. 6 and 6A but taken at 18 months post-operatively with FIG. 7A showing diffuse fibroplasia and FIG. 7 showing more organized columnar orientation of fibroblasts and a more sophisticated fibrocartilage than in FIG. 6.
Figure 8:
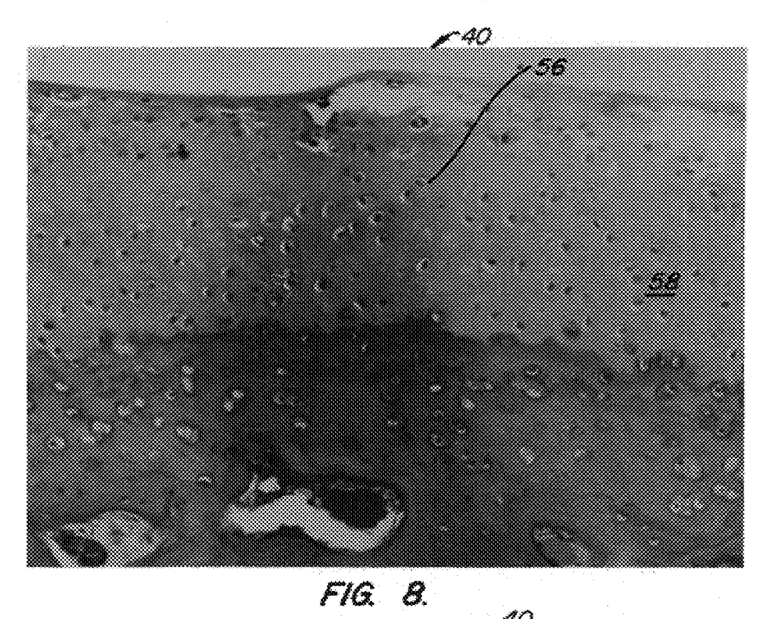
FIGS. 8 and 8A are similar to FIGS. 7 and 7A but taken 24 months post-operatively with FIG. 8A illustrating complete resurfacing of the raw bone of the glenoid and FIG. 8 showing organized chondrocytes and hyaline-like fibrocartilage.

Of even greater significance are the microscopic findings after the glenoid joints 36, 38, 40 of FIGS. 6, 7 and 8 were fixed, stained and prepared on microscopic slides. These were stained with H and E stain. A control glenoid joint 42, see FIG. 4, was also removed to permit the normal, unaltered cartilage to be studied and stained with microscopic slides prepared; these of course revealed normal hyaline cartilage on the joint surface. A second control joint 48, see FIG. 5, was also removed in which the cartilage was removed with power burr 22 creating the original state prior to the opposition of surface 20 against bioresorbable implant 23. Slides of the surface tissue of control joint 48 showed complete absence of all cartilage with just subchondral bone 50 appearing on the slides.

Figure 6A:
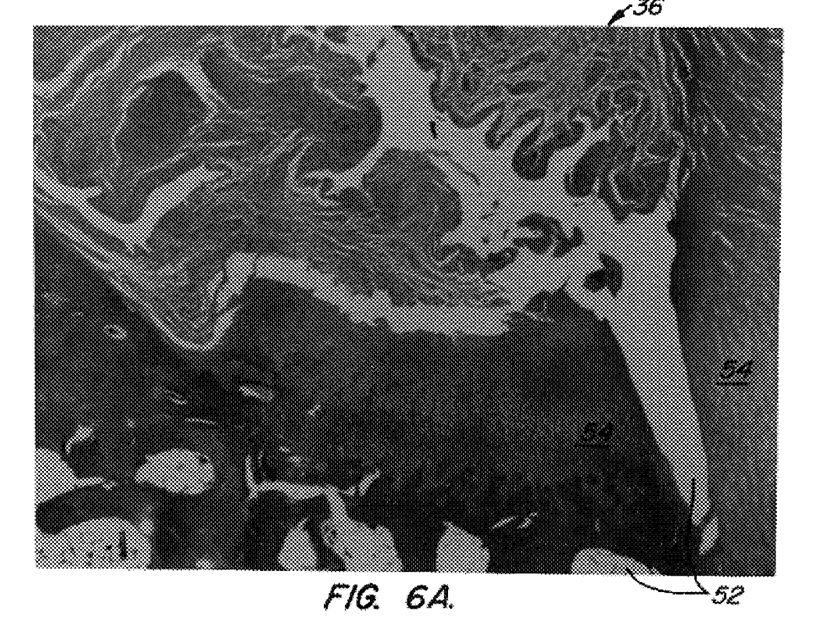

Examination of the slides of the experimental joint studies at one year revealed evidence of definite fibrocartilage 52. See FIGS. 6 and 6A. The blood clot that had formed on the raw bony surface 20 had gradually formed a fibroblast scar which had undergone fibroplasia. There was evidence of fibrocartilage 52, although there was still a significant amount of fibroplasia 54. At 12 months, implant 23 was about 50% absorbed.

Figure 7A:
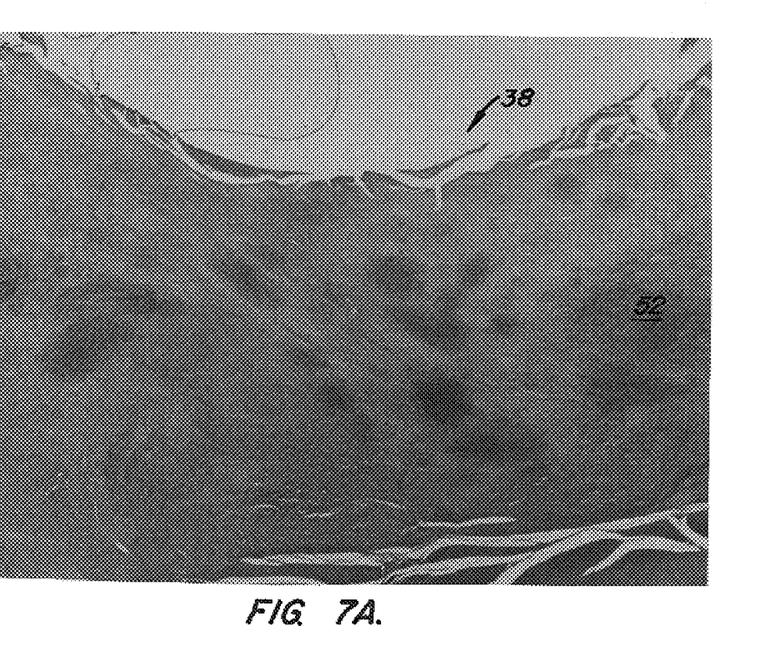

At 18 months, see FIG. 7A, there was a definite progression of this fibroplasia and early fibrocartilage into fibrocartilage 52. At this point implant 23 was about 75% absorbed. FIG. 7, also at 18 months, shows a fibrocartilage joint surface in which the cartilage cell called the chondrocyte 56 now appeared to be developing in a more normal columnar pattern (see FIG. 4) with definite more sophisticated appearance of the joint surface.

Figure 4:
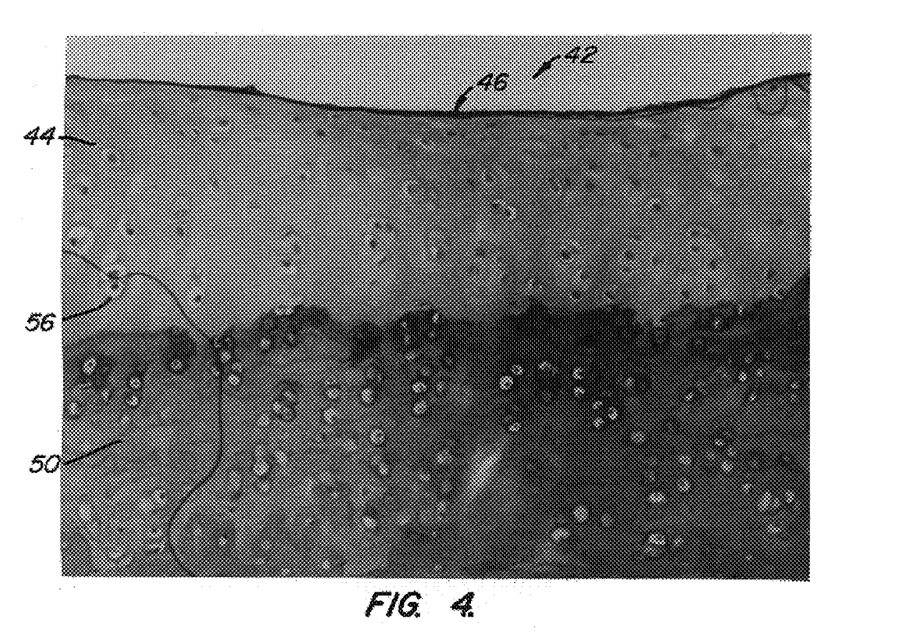
FIG. 4 shows, in cross-section, a normal glenoid articular surface.
Figure 8A:
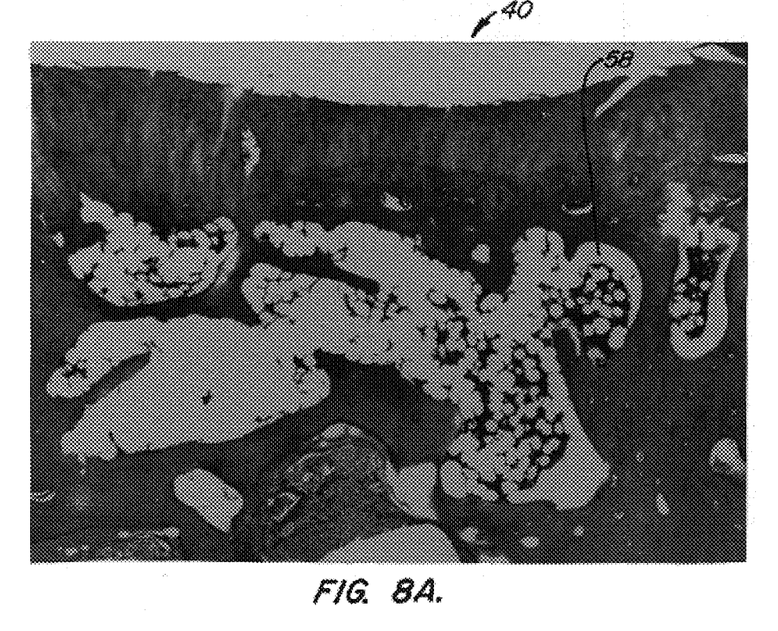

At two years the most remarkable finding was that this advanced form of fibrocartilage 58 now appeared to be progressing to what was determined by microscopic study to have the appearance of actual hyaline cartilage; compare FIGS. 4 and 8. This had never been achieved experimentally before and is a most remarkable finding. FIG. 8A illustrates the complete resurfacing of joint 40 with this advanced, hyaline-like cartilage 58. By this time, implant 23 was effectively entirely absorbed.

The rabbit studies provide experimental support for the concept that a resected joint surface with a bioresorbable inert implant allowed to move against resected surface 20 will stimulate the normal healing process of fibroplasia to fibrocartilage. It is believed that the movement of the resected surface against the implant encourages formation of fibrocartilage. This type of surgical procedure has enormous application in the upper extremity joints, such as at the small joint surfaces of the fingers and the thumb; between the small ball bearing bones of the wrist, the carpal bones; for the distal surface of the radius, the primary wrist joint; and the elbow joint and even the shoulder joint. It is also noted that there are certain joint surfaces in the lower extremity that are non-weight bearing, such as the underside of the knee cap or patella, which can also be resurfaced by a resorbable implant stimulating formation of the fibrocartilage.

While the fibrocartilage 58 created at the resected joint has the appearance of hyaline cartilage, and thus may be suitable for weight-bearing joints, more investigation is needed into this aspect of the invention. Thus, the invention appears especially well suited for substantially non-weight-bearing joints, and may be suited for weight-bearing joints also.

The size and material from which implant 23 is made will be determined by the size and shape of the joint to be treated and the desired speed at which the implant is to be absorbed into the body. Much of this information will necessarily be the result of experimental studies as well as the condition of the particular joint in question. Implant 23 used with the rabbit studies had a smooth head 24 with a diameter of about 9 mm, a maximum thickness of about 1.5 mm and stem length of about 9.5 mm. Stem 26 had a nominal diameter of about 5 mm while the three locking rings 62 formed on stem 26 each had a diameter of about 6 mm. It was desired that resected surface 20 be about the same diameter as head 24. Implant 23 can also be made from bioabsorbable materials other than pure non-porous PLA such as a lactic acid copolymer PLA or PGA.

In the rabbit test both of the ball and socket surfaces were resected. This may not always be necessary. However, what appears to be necessary is that a resected surface must rub against the bioabsorbable implant to create the fibrocartilage. While in the rabbit test the insert was made to fit on humoral head 14, it could also have been configured with a concave outer surface and mounted to resected surface 34 of the socket portion of the ball and socket joint. The preferred embodiment uses an implant having a stem to secure the implant to the joint. In some cases a central stem may not be necessary. For example, a series of small projections might be suitable to ensure that the implant remains in place between the articulated joint surfaces. Stem 26 is designed to be held within cavity 21 through a friction fit. Other designs for holding implant 23 to the joint member, such as through the use of adhesives or barbed projections, could also be used.

Other modifications and variation can be made to the disclosed embodiment and method without departing from the subject of the invention as defined in the following claims.

What is claimed is:

1. A method for treating a joint formed by opposing bones having first and second mating joint surfaces so that relative slidable joint motion between the bones is permanently maintained comprising the following steps:
    removing at least a portion of the first joint surface to expose a cancellous bone surface covered by a layer selected from the group consisting of at least one of blood clot and hematoma;
    selecting an implant made of bioresorbable material only and having a face adapted to face the cancellous bone surface;
    placing the bioresorbable implant between the second joint surface and the cancellous bone surface so that the face is in slidable contact with the layer covering the cancellous bone surface and the implant initially keeps said exposed cancellous bone surface spaced apart from the second joint surface while permitting unrestricted relative slidable motion between the face and the cancellous bone surface including the layer covering it;
    using the joint while allowing resorption of the implant and causing unrestricted slidable motions between the face and the layer covering the cancellous bone surface to stimulate the formation of fibroblast from the layer covering the cancellous bone surface so that the fibroblast can progress into fibrocartilage as the implant is resorbed, the fibrocartilage replaces the implant during such resorption, and thereafter relative slidable motion between the bones along the fibrocartilage occurs when using the joint.

2. The method of claim 1 further comprising the step of selecting the bioresorbable implant made of a polymer of lactic acid.

3. The method of claim 2 wherein the selecting step is carried out by selecting a lactic acid copolymer.

4. The method of claim 1 further comprising the steps of:
    estimating the period time it will take for the fibroblast to progress into fibrocartilage; and
    selecting the bioresorbable implant of a size, shape and material according to said period of time.

5. The method of claim 1 further comprising the step of ensuring the exposed cancellous bone surface and the face of the bioresorbable implant placed against said cancellous bone surface have complementary surface shapes.

6. The method of claim 5 wherein the ensuring step includes the step of selecting curved surface shapes as said complementary surface shapes.

7. A method for treating at least one degenerated surface on a cancellous bone, the cancellous surface being one of first and second relatively slidably movable surfaces defining a non-weight bearing body joint, so that slidable joint motion between the bones is permanently maintained, the method comprising the steps of resecting the bone to form the at least one degenerated cancellous bone surface to expose a layer selected from the group consisting of at least one of blood clot and hematoma thereon, placing an implant made of bioresorbable material only between the at least one degenerated cancellous bone surface and the second surface to thereby space the surfaces apart, providing the implant with at least one face which is opposite and shaped complementary to at least one degenerated cancellous bone surface so that the implant can slidably move without restriction relative to the at least one degenerated cancellous bone surface, allowing the face to slidably move relative to the at least one degenerated cancellous bone surface and the layer selected from the group consisting of at least one of blood clot and hematoma without restriction to thereby stimulate the growth of fibroblast from the layer selected from the group consisting of at least one of blood clot and hematoma on the at least one cancellous surface and the conversion of the fibroblast into fibrocartilage during the allowing step, and gradually resorbing the implant during the allowing step so that, upon resorption of the implant, the fibrocartilage forms at least one of the body joint defining surfaces.

8. A method for treating a non-weight bearing joint having first and second mating joint surfaces so that slidable joint motion between the bones is permanently maintained comprising the following steps:
    removing at least a portion of the first joint surface to generate an exposed cancellous bone surface covered by a layer selected from the group consisting of at least one of blood clot and hematoma;
    placing an implant made of bioresorbable material only between and in contact with the exposed cancellous bone surface and the second joint surface so the implant initially keeps said exposed cancellous bone surface spaced apart from the second joint surface;
    providing the implant with a face which is opposite the exposed cancellous bone surface;
    permitting unrestricted relative slidable motion between the face and the exposed cancellous bone surface;
    using the joint and slidably moving the face relative to the exposed cancellous bone surface and the layer without restriction caused by the implant;
    allowing formation of fibroblast from the layer and of fibrocartilage from the fibroblast while using the joint as the implant is resorbed and continuing to slidably move the face relative to the exposed cancellous bone surface;
    following the complete resorption of the implant continuing to slidably move the second surface along the formed fibrocartilage;
    estimating the period of time it will take for the fibroblast to progress into fibrocartilage; and
    selecting the bioresorbable implant of a size, shape and material according to said period of time.

9. A method for treating a joint having first and second mating joint surfaces carried by cancellous bone so that slidable joint motion between the bones is permanently maintained comprising:
    removing at least a portion of the first joint surface to expose a cancellous bone surface covered by a layer selected from the group consisting of at least one of blood clot and hematoma thereon;
    forming a cavity into the medullary canal of the cancellous bone carrying the second joint surface;

selecting an implant made of bioresorbable material only and configured to fit between the cancellous bone surface and the second joint surface, the implant having a face, a backside and a stem portion extending from the backside and configured to fit within said cavity;

inserting the stem portion into the cavity and placing the bioresorbable implant between the cancellous bone surface and the second joint surface so the implant initially keeps said surfaces spaced apart and the face is freely slidably movable relative to the cancellous bone surface and the layer;

using the joint while allowing complete resorption of the implant and permitting unrestricted relative slidable motion between the face and the cancellous bone surface and the layer; and allowing formation of fibroblast from the layer and of fibrocartilage from the fibroblast while using the joint as the implant is completely resorbed to replace the implant and maintain relative slidable motion between the bones along the formed fibrocartilage.

* * * * *